United States Patent [19]
Park et al.

[11] Patent Number: 5,900,521
[45] Date of Patent: May 4, 1999

[54] CATALYSTS FOR CONVERTING METHANE OR PURIFIED NATURAL GAS, PREPARATION THEREOF, AND PROCESS FOR PREPARATION OF ETHYLENE USING THE CATALYSTS

[75] Inventors: Dae Chul Park, Daejon; Pyung Kwon Ahn, Kwangju, both of Rep. of Korea

[73] Assignee: Korean Research Institute of Chemical Technology, Daejon, Rep. of Korea

[21] Appl. No.: 08/549,718

[22] PCT Filed: May 21, 1994

[86] PCT No.: PCT/KR94/00054

§ 371 Date: Nov. 14, 1995

§ 102(e) Date: Nov. 14, 1995

[87] PCT Pub. No.: WO94/27723

PCT Pub. Date: Dec. 8, 1994

[30] Foreign Application Priority Data

May 22, 1993 [KR]  Rep. of Korea .................. 93-8927

[51] Int. Cl.$^6$ .............................. B01J 31/18; C07C 2/24; C07C 2/26
[52] U.S. Cl. ............................ 585/511; 502/66; 502/74; 502/161; 502/162; 585/513; 585/514; 585/651
[58] Field of Search ...................................... 502/208, 210, 502/213, 66, 74, 211, 161, 162; 585/500, 943, 652, 514, 651, 511, 513; 252/468

[56] References Cited

U.S. PATENT DOCUMENTS

| | | | |
|---|---|---|---|
| 4,255,283 | 3/1981 | Bartek et al. | 252/437 |
| 5,105,053 | 4/1992 | Jacobson et al. | |
| 5,177,294 | 1/1993 | Siriwardane. | |

FOREIGN PATENT DOCUMENTS 2253858  9/1992  United Kingdom.

*Primary Examiner*—Wayne Langel
*Attorney, Agent, or Firm*—Jacobson, Price, Holman & Stern, PLLC

[57] ABSTRACT

Catalysts for preparing ethylene by conversion of methane or purified natural gas and preparation thereof, and process for preparation of ethylene by direct conversion of methane or purified natural gas using said catalysts. The catalysts have the formula I as follows:

$$M_a,P_c/S \qquad (I)$$

wherein, M is a compound selected from the group consisting of $RuCl_2(PPh_3)_3$, $RuCl_2(CO)_2(PPh_3)_2$, $Ru_3(CO)_{12}$, $RhCl(CO)(PPh_3)_2$, $IrCl(CO)PPh_3)_3$, $Pd(PPh_3)_4$, $Pt(PPh_3)_4$ and $RuCl_3.xH_2O$, S is an inorganic carrier selected from the group consisting of $\alpha$-$Al_2O_3$, $\gamma$-$Al_2O_3$, $SiO_2$, $SiO_2$-$Al_2O_3$, Y-zeolite, MgO and $TiO_2$, and P is a phosphorus compound promoter selected from the group consisting of $PPh_3$, $P(OCH_3)_3$, $P(OC_2H_5)_3$, and $P(O)(OC_2H_5)_3$; wherein a is the amount of metal in the catalyst, ranging from 0.25 to 5 wt % of the catalyst and c is the amount of promoter in the catalyst, ranging from 1.0 to 20.0 wt % of the catalyst.

5 Claims, No Drawings

CATALYSTS FOR CONVERTING METHANE OR PURIFIED NATURAL GAS, PREPARATION THEREOF, AND PROCESS FOR PREPARATION OF ETHYLENE USING THE CATALYSTS

FIELD OF THE INVENTION

The present invention relates to catalysts supported on inorganic carriers, for producing ethylene which is used in basic reactions including polymerization, copolymerization and polycondensation reactions in the petrochemical industry and fine chemicals industry, and preparation of the catalysts having the following formula:

$$Ma,Pc/S \quad \text{Formula (I)}$$

In Ma,Pc/S formula (I), M is a compound selected from the group consisting of $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$ and $RuCl_3 \cdot xH_2O$; S is an inorganic carrier selected from the group consisting of $\alpha\text{-}Al_2O_3$, $\gamma\text{-}Al_2O_3$, $SiO_2$, $SiO_2\text{-}Al_2O_3$, Y-zeolite, MgO and $TiO_2$; P is a promoter selected from the group consisting of $PPh_3$, $P(OCH_3)_3$, $P(OC_2H_5)_3$ and $P(O)(OC_2H_5)_3$; a is the amount of metal in the catalyst in weight percent, ranging from 0.25 to 5 wt %; and c is the amount of promoter in the catalyst in weight percent, ranging from 1.0 to 20.0 weight percent.

Further, the present invention provides a new process for the preparation of ethylene by directly converting methane or purified natural gas, in the presence of the above catalyst with nitrogen, at a temperature of about 670 to 850° C., preferably in the range of 710 to 810° C., which is a distinctly lower reaction temperature compared to that used for the conventional synthesis of hydrocarbon(s) by dehydrogenation. By the process of the present invention, ethylene is obtained in a short time, with a high yield, and without by-products, such as CO, $CO_2$, contrary to oxidative coupling reactions where oxygen is introduced.

BACKGROUND

There are very few processes known in the art which use a catalyst to produce ethylene by direct conversion of methane; moreover, what is known is in a different technical field from the present invention. In conventional processes, large amounts of by-product such as carbon dioxide are produced, separation and removal thereof is difficult and environmental pollution is likely to be caused. Also, synthesis of hydrocarbon(s) by conventional dehydrogenation is conducted at relatively high temperatures, i.e., about 1500 to 1550° C. via thermal or electric cracking reactions which require a high energy supply, expensive high temperature equipment (plan), as well as running at an enormous loss of thermal energy, which is costly, such as severe corrosion of the reactor.

Various patents which describe synthesis of hydrocarbon (s) by oxidative coupling or dehydrogenation reactions, include U.S. Pat. Nos. 5066629, 5068486 and 5118654, Canadian Patent No. 2016675 and Japanese Patent Nos. 04352730, 04368342.

SUMMARY OF THE INVENTION

Until now, new catalysts being able to conduct conversion reaction not at so (ultra) high temperature as that in process for synthesis of hydrocarbons by dehydrogenation but at distinctly lower (mid.low) temperature, and new process for producing said catalyst, and new process for conversion into ethylene using said catalyst have always been expected.

To meet the expectations above, resulting from years of study, the inventors have developed a new catalyst and a simple process for obtaining ethylene in a short time, with high yield and with trace amounts of impurities, by converting methane or purified natural gas in the presence of said catalyst at distinctly lower temperatures compared to that used for the synthesis of hydrocarbon(s) by dehydrogenation or oxidative coupling reactions. Thus, by the present invention, the direct conversion of methane carried out at distinctly low temperatures enables costs associated with enormous amounts of thermal energy that was needed in the synthesis of hydrocarbon(s) by dehydrogenation or oxidative coupling reactions to be saved, and minimizes environmental pollution by reducing the amount of impurities, namely $CO_2$, produced. By the present invention a method for preparing the new catalyst is also provided.

DETAILED DESCRIPTION OF THE INVENTION

The present invention will be described in further detail with reference to Examples.

First, the catalyst is produced by supporting a metal complex and a promoter on an inorganic carrier.

By the present invention, the synthesis and purification of the catalyst is much easier than other processes.

Through development of the catalyst of the present invention, reaction conditions such as reaction temperature, reaction pressure are mitigated considerably and ethylene is produced with a high yield.

Furthermore, due to the development of the process of using the catalyst of the present invention, the process for the preparation of ethylene is simplified, and as a result, productivity is enhanced.

The present invention is described in detail as follows.

In the present invention, by developing a new process where methane or purified natural gas is converted directly to ethylene, the overall process for preparing ethylene is simplified. Other advantages of the present invention include the use of a lower reaction temperature, i.e., the temperature is lowered to about 670 to 850° C., preferably in the range of 710 to 810° C., and the amount of impurities, such as carbon dioxide, are greatly reduced.

In the present invention, by adding triphenylphospine as a promoter to a complex containing Ru, such as $RuCl_2(PPh_3)_3$ and $RuCl_2(CO)_2(PPh_3)_2$, ethylene is produced with a high yield, at a temperature of about 810° C. At this time, the conversion rate is maintained within the range of about 8 to 12% and through continuous recirculation of the raw material introduced, the conversion rate is maximized.

That is to say, through solid surface reaction using a supported Ru complex catalyst, reaction conditions such as reaction temperature and pressure are considerably mitigated, and at the same time, the reaction equipment is simplified.

The process for preparing a catalyst supported on inorganic carriers of the present invention is as follows.

Metal cluster (compound) and organic metal complex are dissolved in mixed solvent consisting of dichloromethane and acetone.

Then, inorganic carrier is added to this solution, and metal cluster (compound) and organic metal complex are immersed into inorganic carrier by stirring at about 20 to 200° C., then dried in a vacuum drier to prepare the catalyst.

Examples of inorganic carriers used are $\alpha\text{-}Al_2O_3$, $\gamma\text{-}Al_2O_3$, $SiO_2$, $SiO_2\text{-}Al_2O_3$, Y-zeolite, MgO and $TiO_2$.

Examples of metal cluster (compound) and organic metal complex compounds used are $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$ and $RuCl_3 \cdot xH_2O$.

According to the experiments of the present invention, the optimum inorganic carriers for preparation of ethylene are $\alpha$-$Al_2O_3$ and MgO, and metal complexes containing metals of group VIII most preferably, Ru and Rh.

The reaction conditions in the presence of the catalyst of the present invention are as follows.

The dilution ratio of nitrogen to methane or purified natural gas is 1 to 6, preferably 1 to 3, based on methane.

The reaction temperature is about 670 to 850° C., preferably in the range of 710 to 810° C.

The concentration of the catalyst is below 5.0 wt %, preferably 1 to 3 wt %.

The space velocity of source gas is about 75 to 1200 $hr^{-1}$, preferably in the range of 150 to 600 $hr^{-1}$.

The reaction pressure is usually about 1 to 5 atm, preferably normal or atmospheric pressure.

The conversion range of methane or purified natural gas, and yield and selectivity of ethylene, are defined as follows.

$$\text{conversion rate (mol \%)} = \frac{\text{mol numbers of methane reacted}}{\text{mol numbers of methane supplied}} \times 100$$

$$\text{yield (mol \%)} = \frac{\text{mol numbers of } C_2 \text{ hydrocarbon such as ethylene produced}}{\text{mol numbers of methane supplied}} \times 100$$

$$\text{selectivity (mol \%)} = \frac{\text{mol numbers of } C_2 \text{ hydrocarbon such as ethylene produced}}{\text{mol numbers of methane reacted}} \times 100$$

or, $$\text{conversion rate (mol \%)} = \frac{\text{mol numbers of methane in purified natural gas reacted}}{\text{mol numbers of methane in purified natural gas supplied}} \times 100$$

$$\text{yield (mol \%)} = \frac{\text{mol numbers of } C_2 \text{ hydrocarbon compound such as ethylene produced}}{\text{mol numbers of methane in purified natural gas supplied}} \times 100$$

$$\text{selectivity (mol \%)} = \frac{\text{mol numbers of } C_2 \text{ hydrocarbon compound such as ethylene produced}}{\text{mol numbers of methane in purified natural gas reacted}} \times 100$$

Reactants and produced are analyzed by gas chromatography.

Examples 1 to 11 relate to the catalyst of the present invention and process for preparation thereof. Examples 12 to 22 relate to the process for producing ethylene by conversion of methane or purified natural gas, in the presence of the catalyst of the present invention.

EXAMPLE 1

$\alpha$-$Al_2O_3$ 5.16 g, $RuCl_2(PPh_3)_3$ 1.00 g (1.04 mmol) and $PPh_3$ 1.09 g (4.16 mmol) are added to mixed solvent consisting of 20 ml of dichloromethane and 10 ml of acetone. This suspension is stirred for about 30 minutes, at a temperature of around 40° C., and evaporated to dryness by distillation under reduced pressure, then dried in a vacuum drier for about 20 hours to prepare a $RuCl_2(PPh_3)_3 \cdot PPh_3/\alpha$-$Al_2O_3$ catalyst.

EXAMPLE 2

$RuCl_2(CO)_2(PPh_3)_2$ 0.56 g (0.744 mol) and $PPh_3$ 0.78 g (2.97 mmol) are added to mixed solvent consisting of 40 ml of dichloromethane and 10 ml of acetone and dissolved, then $\alpha$—$Al_2O_3$ 3.68 g is added thereto. This suspension is stirred for about 30 minutes, at a temperature of around 40° C., and solvent is evaporated by distillation under reduced pressure. The residue obtained is dried in a vacuum drier for about 20 hours to prepare a $RuCl_2(CO)_2(PPh_3)_2 \cdot PPh_3/\alpha$-$Al_2O_3$ catalyst.

EXAMPLE 3

$\alpha$-$Al_2O_3$ 3.95 g, $Ru_3(CO)_{12}$ 0.17 g (0.266 mmol) and $PPh_3$ 0.09 g (0.343 mmol) are added to mixed solvent consisting of 10 ml of dichloromethane and 100 ml of acetone and dissolved.

This suspension is stirred for about 30 minutes, at a temperature of around 40° C., and solvent is evaporated by distillation under reduced pressure.

The residue obtained is dried in a vacuum drier for about 20 hours to prepare a $Ru_3(CO)_{12} \cdot PPh_3/\alpha$-$Al_2O_3$ catalyst.

EXAMPLE 4

$\alpha$-$Al_2O_3$ 3.28 g, $RhCl(CO)(PPh_3)_2$ 0.45 g (0.652 mmol) and $PPh_3$ 0.68 g (2.59 mmol) are added to mixed solvent consisting of 10 ml of dichloromethane and 30 ml of acetone and dissolved.

This suspension is stirred for about 30 minutes, at a temperature of around 40° C., and solvent is evaporated by distillation under reduced pressure.

The residue obtained is dried in a vacuum drier for about 20 hours to prepare a $RhCl(CO)(PPh_3)_2 \cdot PPh_3/\alpha$-$Al_2O_3$ catalyst.

EXAMPLE 5

$\alpha$-$Al_2O_3$ 3.14 g, $IrCl(CO)(PPh_3)_2$ 0.26 g (0.333 mmol), and $PPh_3$ 0.35 g (1.33 mmol) are added to mixed solvent consisting of 60 ml of dichloromethane and 10 ml of acetone and dissolved.

This suspension is stirred for about 30 minutes, at a temperature of around 40° C., and solvent is evaporated by distillation under reduced pressure.

The residue obtained is dried in a vacuum drier for about 20 hours to prepare a $IrCl(CO)(PPh_3)_2 \cdot PPh_3/\alpha$-$Al_2O_3$ catalyst.

EXAMPLE 6

$\alpha$-$Al_2O_3$ 3.7 g, $Pd(PPh_3)_4$ 0.84 g (0.727 mmol) and $PPh_3$ 0.76 g (2.90 mmol) are added to mixed solvent consisting of 30 ml of dichloromethane and 10 ml of acetone and dissolved.

This suspension is stirred for about 30 minutes, at a temperature of around 40° C., and solvent is evaporated by distillation under reduced pressure.

The residue obtained is dried in a vacuum drier for about 20 hours to prepare a $Pd(PPh_3)_4 \cdot PPh_3/\alpha$-$Al_2O_3$ catalyst.

EXAMPLE 7

α-$Al_2O_3$ 4.45 g, $Pt(PPh_3)_4$ 0.58 g (0.466 mmol) and $PPh_3$ 0.49 g (1.87 mmol) are added to mixed solvent consisting of 30 ml of dichloromethane and 10 ml of acetone and dissolved.

This suspension is stirred for about 30 minutes, at a temperature of around 40° C., and solvent is evaporated by distillation under reduced pressure.

The residue obtained is dried in a vacuum drier for about 20 hours to prepare a $Pt(PPh_3)_4.PPh_3/α-Al_2O_3$ catalyst.

EXAMPLE 8

Except for using MgO 4.39 g and $PPh_3$ 0.93 g (3.55 mmol) as inorganic carrier and promoter, respectively, Example 1 is repeated to prepare a $RuCl_2(PPh_3)_3.PPh_3/MgO$ catalyst.

EXAMPLE 9

Except for using $RuCl_2(PPh_3)_3$ 0.25 g (0.261 mmol, 0.5 wt % Ru) and $PPh_3$ 0.27 g (1.03 mmol), Example 1 is repeated to prepare a $RuCl_2(PPh_3)_3\ PPh_3./α-Al_2O_3$ catalyst.

EXAMPLE 10

Except for $RuCl_2(PPh_3)_3$ 1.0 g (1.04 mmol, 4.0 wt % Ru) and $PPh_3$ 1.09 g (4.16 mmol), Example 1 is repeated to prepare a $RuCl_2(PPh_3)_3.PPh_3/α-Al_2O_3$ catalyst.

EXAMPLE 11

α-$Al_2O_3$ 5.01 g, $RuCl_3.xH_2O$ 0.21 g (1.012 mmol) and $PPh_3$ 1.06 g (4.04 mmol) are added to mixed solvent consisting of 20 ml of dichloromethane and 10 ml of acetone and stirred for about 30 minutes, at a temperature of around 40° C. This suspension is evaporated to dryness by distillation under reduced pressure, then dried in a vacuum drier for about 20 hours to prepare a $RuCl_3.xH_2O.PPh_3/α-Al_2O_3$ catalyst.

The catalysts prepared were analyzed and the results of the analysis are given in the following tables. The results presented for Examples 12 to 22 are approximate values.

In the case of temperatures, they are surrounding temperatures based on given value.

EXAMPLE 12

Methane (or purified natural gas) and nitrogen are introduced, each at a flow rate of 10 ml/min, into a continuous stationary phase flow reactor (inner diameter: 0.70 cm; length: 40 cm; equipment: stainless steel 316) in the presence of the catalyst $RuCl_2(PPh_3)_3.PPh_3/α-Al_2O_3$ (2 wt % Ru) prepared according to Example 1. Products are obtained by continuous reaction under normal pressure (about 1 atm) at each reaction temperature and analyzed by gas chromatography, the results of which are presented in Table 1 (from Example 12 to Example 22, the raw material is continuously reintroduced into the conversion reaction).

TABLE 1

| Reaction Temp. | Conversion | Yield (%) | | Selectivity (%) | |
| --- | --- | --- | --- | --- | --- |
| *(° C.) | (%) | Ethylene | Ethane | Ethylene | Ethane |
| 710 | 2.2 | 1.4 | 0.8 | 63.6 | 36.4 |
| 730 | 3.6 | 2.5 | 1.1 | 69.4 | 30.6 |

TABLE 1-continued

| Reaction Temp. | Conversion | Yield (%) | | Selectivity (%) | |
| --- | --- | --- | --- | --- | --- |
| *(° C.) | (%) | Ethylene | Ethane | Ethylene | Ethane |
| 750 | 4.9 | 3.9 | 1.0 | 79.6 | 20.4 |
| 770 | 6.0 | 5.3 | 0.7 | 88.3 | 11.7 |
| 790 | 8.6 | 7.7 | 0.9 | 89.5 | 10.5 |
| 810 | 12.1 | 11.0 | 1.1 | 90.9 | 9.1 |

EXAMPLE 13

Except for using $RuCl_2(CO)_2(PPh_3)_2.PPh_3/α-Al_2O_3$ as the catalyst, Example 12 is repeated and an analysis of the resulting products is presented in Table 2.

TABLE 2

| Reaction Temp. | Conversion | Yield (%) | | Selectivity (%) | |
| --- | --- | --- | --- | --- | --- |
| *(° C.) | (%) | Ethylene | Ethane | Ethylene | Ethane |
| 710 | 2.8 | 1.9 | 0.9 | 67.9 | 32.1 |
| 730 | 3.8 | 3.0 | 0.8 | 78.9 | 21.1 |
| 750 | 4.6 | 4.0 | 0.6 | 87.0 | 13.0 |
| 770 | 5.4 | 4.8 | 0.6 | 88.9 | 11.1 |
| 790 | 6.6 | 5.9 | 0.7 | 89.4 | 10.6 |
| 810 | 8.6 | 7.7 | 0.9 | 89.5 | 10.5 |

EXAMPLE 14

Except for using $Ru_3(CO)_{12}.PPh_3/α-Al_2O_3$ (2 wt % Ru) as the catalyst, Example 12 is repeated and an analysis of the resulting products is presented in Table 3.

TABLE 3

| Reaction Temp. | Conversion | Yield (%) | | Selectivity (%) | |
| --- | --- | --- | --- | --- | --- |
| *(° C.) | (%) | Ethylene | Ethane | Ethylene | Ethane |
| 710 | 2.4 | 1.7 | 0.7 | 70.8 | 29.2 |
| 730 | 3.5 | 2.9 | 0.6 | 82.9 | 17.1 |
| 750 | 4.6 | 4.0 | 0.6 | 87.0 | 13.0 |
| 770 | 5.4 | 4.8 | 0.6 | 88.9 | 11.1 |
| 790 | 6.8 | 6.2 | 0.6 | 91.2 | 8.8 |
| 810 | 8.3 | 7.8 | 0.5 | 94.0 | 6.0 |

EXAMPLE 15

Except for using $RuCl(CO)(PPh_3)_2.PPh_3/α-Al_2O_3$ (2 wt % Ru) as the catalyst, Example 12 is repeated and an analysis of the resulting products is presented in Table 4.

TABLE 4

| Reaction Temp. | Conversion | Yield (%) | | Selectivity (%) | |
| --- | --- | --- | --- | --- | --- |
| *(° C.) | (%) | Ethylene | Ethane | Ethylene | Ethane |
| 710 | 2.2 | 1.2 | 1.0 | 54.5 | 45.5 |
| 730 | 2.6 | 1.8 | 0.8 | 69.2 | 30.8 |
| 750 | 4.4 | 3.4 | 1.0 | 77.3 | 22.7 |

TABLE 4-continued

| Reaction Temp. | Conversion | Yield (%) | | Selectivity (%) | |
|---|---|---|---|---|---|
| *(° C.) | (%) | Ethylene | Ethane | Ethylene | Ethane |
| 770 | 5.5 | 4.7 | 0.8 | 85.5 | 14.5 |
| 790 | 6.7 | 6.0 | 0.7 | 89.6 | 10.4 |
| 810 | 8.5 | 7.8 | 0.7 | 91.8 | 8.2 |

EXAMPLE 16

Except for using IrCl(CO)(PPh$_3$)$_2$.PPh$_3$/α-Al$_2$O$_3$ (2 wt % Ir) as the catalyst, Example 12 is repeated and an analysis of the resulting products is presented in Table 5.

TABLE 5

| Reaction Temp. | Conversion | Yield (%) | | Selectivity (%) | |
|---|---|---|---|---|---|
| *(° C.) | (%) | Ethylene | Ethane | Ethylene | Ethane |
| 710 | 2.0 | 1.2 | 0.8 | 60.0 | 40.0 |
| 730 | 3.1 | 2.3 | 0.8 | 74.2 | 25.8 |
| 750 | 4.5 | 3.7 | 0.8 | 82.2 | 17.8 |
| 770 | 5.2 | 4.5 | 0.7 | 86.5 | 13.5 |
| 790 | 6.6 | 5.9 | 0.7 | 89.4 | 10.6 |
| 810 | 8.2 | 7.6 | 0.6 | 92.7 | 7.3 |

EXAMPLE 17

Except for using Pd(PPh$_3$)$_4$.PPh$_3$/α-Al$_2$O$_3$ (2 wt % Pd) as the catalyst, Example 12 is repeated and an analysis of the resulting products is presented in Table 6.

TABLE 6

| Reaction Temp. | Conversion | Yield (%) | | Selectivity (%) | |
|---|---|---|---|---|---|
| *(° C.) | (%) | Ethylene | Ethane | Ethylene | Ethane |
| 710 | 1.7 | 1.1 | 0.6 | 64.7 | 35.3 |
| 730 | 2.6 | 2.0 | 0.6 | 76.9 | 23.1 |
| 750 | 4.1 | 3.4 | 0.7 | 82.9 | 17.1 |
| 770 | 5.5 | 4.8 | 0.7 | 87.3 | 12.7 |
| 790 | 6.7 | 6.0 | 0.7 | 89.6 | 10.4 |
| 810 | 8.6 | 7.9 | 0.7 | 91.9 | 8.1 |

EXAMPLE 18

Except for using Pt(PPh$_3$)$_4$.PPh$_3$/α-Al$_2$O$_3$ (2 wt % Pt) as the catalyst, Example 12 is repeated and an analysis of the resulting products is presented in Table 7.

TABLE 7

| Reaction Temp. | Conversion | Yield (%) | | Selectivity (%) | |
|---|---|---|---|---|---|
| *(° C.) | (%) | Ethylene | Ethane | Ethylene | Ethane |
| 710 | 1.1 | 0.7 | 0.4 | 63.6 | 36.4 |
| 730 | 2.2 | 1.5 | 0.7 | 68.2 | 31.8 |
| 750 | 3.2 | 2.5 | 0.7 | 78.1 | 21.9 |
| 770 | 4.7 | 4.0 | 0.7 | 85.1 | 14.9 |
| 790 | 6.0 | 5.4 | 0.6 | 90.0 | 10.0 |
| 810 | 7.5 | 7.0 | 0.5 | 93.0 | 6.7 |

EXAMPLE 19

Except for using RuCl$_2$(PPh$_3$)$_3$.PPh$_3$/MgO (2 wt % Ru) as the catalyst, Example 12 is repeated and an analysis of the resulting products is presented in Table 8.

TABLE 8

| Reaction Temp. | Conversion | Yield (%) | | Selectivity (%) | |
|---|---|---|---|---|---|
| *(° C.) | (%) | Ethylene | Ethane | Ethylene | Ethane |
| 710 | 2.3 | 1.3 | 1.0 | 56.5 | 43.5 |
| 730 | 3.2 | 2.2 | 1.0 | 68.8 | 31.2 |
| 750 | 4.1 | 3.3 | 0.8 | 80.5 | 19.5 |
| 770 | 4.4 | 3.6 | 0.8 | 81.8 | 18.2 |
| 790 | 6.3 | 5.5 | 0.8 | 87.3 | 12.7 |
| 810 | 6.4 | 5.9 | 0.5 | 92.2 | 7.8 |

EXAMPLE 20

Except for using RuCl$_2$(PPh$_3$)$_3$.$_{PPh3}$/α-Al$_2$O$_3$ (0.5 wt % Ru) as the catalyst, Example 12 is repeated and an analysis of the resulting products is presented in Table 9.

TABLE 9

| Reaction Temp. | Conversion | Yield (%) | | Selectivity (%) | |
|---|---|---|---|---|---|
| *(° C.) | (%) | Ethylene | Ethane | Ethylene | Ethane |
| 710 | 1.3 | 0.7 | 0.6 | 53.8 | 46.2 |
| 730 | 1.9 | 1.2 | 0.7 | 63.2 | 36.8 |
| 750 | 3.0 | 2.3 | 0.7 | 76.6 | 23.4 |
| 770 | 4.6 | 3.9 | 0.7 | 84.8 | 15.2 |
| 790 | 7.1 | 6.4 | 0.7 | 90.1 | 9.9 |
| 810 | 8.2 | 7.5 | 0.7 | 91.5 | 8.5 |

EXAMPLE 21

Except for using RuCl$_2$(PPh$_3$)$_3$.PPh$_3$/α-Al$_2$O$_3$ (4.0 wt % Ru) as the catalyst, Example 12 is repeated and an analysis of the resulting products is presented in Table 10.

TABLE 10

| Reaction Temp. | Conversion | Yield (%) | | Selectivity (%) | |
|---|---|---|---|---|---|
| *(° C.) | (%) | Ethylene | Ethane | Ethylene | Ethane |
| 710 | 2.4 | 1.6 | 1.0 | 66.7 | 33.3 |
| 730 | 3.5 | 2.5 | 1.0 | 71.4 | 28.6 |
| 750 | 4.9 | 3.9 | 1.0 | 79.6 | 20.4 |
| 770 | 6.3 | 5.4 | 0.9 | 85.7 | 14.3 |
| 790 | 7.7 | 6.8 | 0.9 | 88.3 | 11.7 |
| 810 | 10.5 | 9.6 | 0.9 | 91.4 | 8.6 |

EXAMPLE 22

Except for using RuCl$_3$.xH$_2$O ·PPh$_3$/α-Al$_2$O$_3$ (2 wt % Ru) as the catalyst, Example 12 is repeated and an analysis of the resulting products is presented in Table 11.

TABLE 11

| Reaction Temp. *(° C.) | Conversion (%) | Yield (%) Ethylene | Yield (%) Ethane | Selectivity (%) Ethylene | Selectivity (%) Ethane |
|---|---|---|---|---|---|
| 710 | 0.4 | 0.0 | 0.4 | 0.0 | 100.0 |
| 730 | 1.1 | 0.5 | 0.6 | 45.5 | 54.5 |
| 750 | 1.8 | 0.9 | 0.9 | 50.0 | 50.0 |
| 770 | 2.6 | 1.7 | 0.9 | 65.4 | 34.6 |
| 790 | 4.4 | 3.5 | 0.9 | 79.5 | 20.5 |

What is claimed is:

1. A catalyst for preparing ethylene by conversion of methane or purified natural gas; said catalyst prepared has the general formula:

$$M_a, P_c/S \qquad (I)$$

wherein, M is a compound selected from the group consisting of $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$ and $RuCl_3 \cdot xH_2O$; S is an inorganic carrier selected from the group consisting of $\alpha$-$Al_2O_3$, $\gamma$-$Al_2O_3$, $SiO_2$, $SiO_2$-$Al_2O_3$, Y-zeolite, MgO and $TiO_2$; and P is a phosphorous compound which is a promoter selected from the group consisting of $PPh_3$, $P(OCH_3)_3$, $P(OC_2H_{15})_3$ and $P(O)(OC_2H_5)_3$; wherein a is the amount of M corresponding to 0.25 to 5 wt % of the catalyst; and c is the amount of P corresponding to 1.0 to 20.0 of the catalyst and wherein M and P are supported on the inorganic carrier, S.

2. A process for preparing a catalyst, which comprises the steps of: (a) adding M, P and S to a single or mixed solvent of dichloromethane and acetone to obtain a suspension; (b) reflux-stirring the suspension at a temperature of about 30 to 250° C.; (c) then, evaporating the solvent by distillation under reduced pressure thereby obtaining a residue; and (d) vacuum drying the residue obtained; wherein said catalyst prepared has the general formula:

$$M_a, P_c/S \qquad (I)$$

wherein, M is a compound selected from the group consisting of $RuCl_2(PPh_3)_3$, $RuCl_2(CO)_2(PPh_3)_2$, $Ru_3(CO)_{12}$, $RhCl(CO)(PPh_3)_2$, $IrCl(CO)(PPh_3)_2$, $Pd(PPh_3)_4$, $Pt(PPh_3)_4$ and $RuCl_3 \cdot xH_2O$; S is an inorganic carrier selected from the group consisting of $\alpha$-$Al_2O_3$, $\gamma$-$Al_2O_3$, $SiO_2$, $SiO_2$-$Al_2O_3$, Y-zeolite, MgO and $TiO_2$; and P is a phosphorous compound which is a promoter selected from the group consisting of $PPh_3$, $P(OCH_3)_3$, $P(OC_2H_{15})_3$ and $P(O)(OC_2H_5)_3$; wherein a is the amount of M corresponding to 0.25 to 5 wt % of the catalyst; and c is the amount of P corresponding to 1.0 to 20.0 wt % of the catalyst and wherein M and P are supported on the inorganic carrier, S.

3. The process according to claim 2, wherein the suspension is reflux-stirred at a temperature of between 40 to 150° C.

4. A process for preparing ethylene, comprising the steps of: (a) reacting methane or purified natural gas and nitrogen, in the presence of the catalyst of claim 1, at a temperature of about 670 to 850° C. and under a pressure of 1 to 5 atm; and (b) obtaining the ethylene produced.

5. A process for preparing ethylene by direct conversion reaction, comprising the steps of: (a) reacting methane or purified natural gas and nitrogen, in the presence of the catalyst of claim 1, at a temperature of about 670 to 850° C. and under a pressure of 1 to 5 atm; and (b) obtaining the ethylene produced; wherein said process does not require the addition of oxygen and carbon dioxide is not generated.

* * * * *